United States Patent [19]

Mercolino et al.

[11] Patent Number: 5,369,036
[45] Date of Patent: Nov. 29, 1994

[54] ENHANCEMENT OF SIGNAL IN IMMUNOASSAYS USING MICROPARTICLES WHICH CONTAIN DIFFERENT DETECTABLE SUBSTANCES

[75] Inventors: Thomas J. Mercolino, Stockton, N.J.; Joanne H. Hasskamp; Edward C. McFarland, both of Baltimore, Md.

[73] Assignee: Becton, Dickinson and Company, Franklin Lakes, N.J.

[21] Appl. No.: 908,136

[22] Filed: Jul. 2, 1992

[51] Int. Cl.$^5$ .......................................... G01N 33/543
[52] U.S. Cl. .................................... 436/523; 436/518; 436/525; 436/528; 436/531; 436/534; 436/800; 436/829; 435/973
[58] Field of Search ............... 436/518, 523, 525, 528, 436/531, 534, 800, 829, 808, 822; 435/973

[56] References Cited

U.S. PATENT DOCUMENTS

| | | | |
|---|---|---|---|
| 4,663,277 | 5/1987 | Wang | 435/5 |
| 4,695,554 | 9/1987 | O'Connell et al. | 436/528 |
| 4,703,017 | 10/1987 | Campbell et al. | 436/501 |
| 4,745,075 | 5/1988 | Hadfield et al. | 436/523 |
| 4,920,046 | 4/1990 | McFarland et al. | 436/518 X |
| 4,960,713 | 12/1990 | Hadfield et al. | 436/523 |
| 4,978,625 | 12/1990 | Wagner | 436/518 |

FOREIGN PATENT DOCUMENTS 9002334 3/1990 WIPO ................ 435/7.24

OTHER PUBLICATIONS

Ho et al., "Immunoliposome Assays: Perspectives, Progress and Potential", in *Liposomes as Drug Carriers,* Gregory Gregoriadis, Ed., John Wiley & Sons, New York, (1988), pp. 527–547.

*Primary Examiner*—Esther M. Kepplinger
*Assistant Examiner*—Susan C. Wolski
*Attorney, Agent, or Firm*—Bruce S. Weintraub

[57] ABSTRACT

A process for assaying at least one analyte uses a tracer which includes multiple detectable substances. A tracer composition includes at least one ligand labeled with a particulate label, the particulate label containing at least one detectable substance. Two or more detectable substances in the assay may be in the same particulate label or in different particulate labels conjugated to different ligands.

2 Claims, 6 Drawing Sheets

ENHANCEMENT OF SIGNAL IN IMMUNOASSAYS USING MICROPARTICLES WHICH CONTAIN DIFFERENT DETECTABLE SUBSTANCES

BACKGROUND OF THE INVENTION

1. Field of the Invention

This invention relates to binding assays, particularly immunoassays, using a detection system with more than one detectable substance.

2. Brief Description of the Prior Art

Problems confronting the art of immunoassays have included the difficulty of simultaneous detection of more than one analyte, a need for detectable labels to measure analytes, a need for good visual determination of label with or without instrumentation, a need for discrimination of signal above noise if instrumentation is used and a need for increased sensitivity.

To increase sensitivity and allow visual detection in assays, analytes, that is, antibodies, antigens or haptens, have been labeled with dyes or fluorochromes. For example, U.S. Pat. No. 4,695,554 describes sacs or liposomes containing a single dye for use in immunoassays.

U.S. Pat. No. 4,703,017, the entire disclosure of which is herein incorporated by reference, describes a solid phase assay using a single colored particulate label such as a liposome including a dye.

U.S. Pat. No. 4,745,075 describes agglutination assays using two or more insoluble colored particles such as non-viable bacterial cells, alginate particles, sepharose beads, silica, alumina, erythrocytes and polymer latexes. The particles are adapted to form different colored agglutinates depending on the presence of specific ligands.

As is known by the skilled artisan, agglutination assays, e.g. the Weil-Felix Test, the Latex Particle Test, agglutinations mediated by lectins or by fibrinogen, etc., do not use solid supports. Agglutination assays use visual and microscopic detection of aggregates which are suspended or aggregated.

There is need for a more sensitive assay than one which relies on a single colored particulate label or color related agglutination. A technique for the enhancement of signal has now been discovered through the use of multi-colored particulate labels in an assay which utilizes a solid support.

SUMMARY OF THE INVENTION

The invention is a process for assaying for at least one analyte. The analyte and a tracer are contacted with a binder on a support under assay conditions. The tracer comprises at least one particulate label connected to at least one ligand, the particulate label including at least one detectable substance. The tracer includes at least two detectable substances which are preferably dyes.

Figure 1:
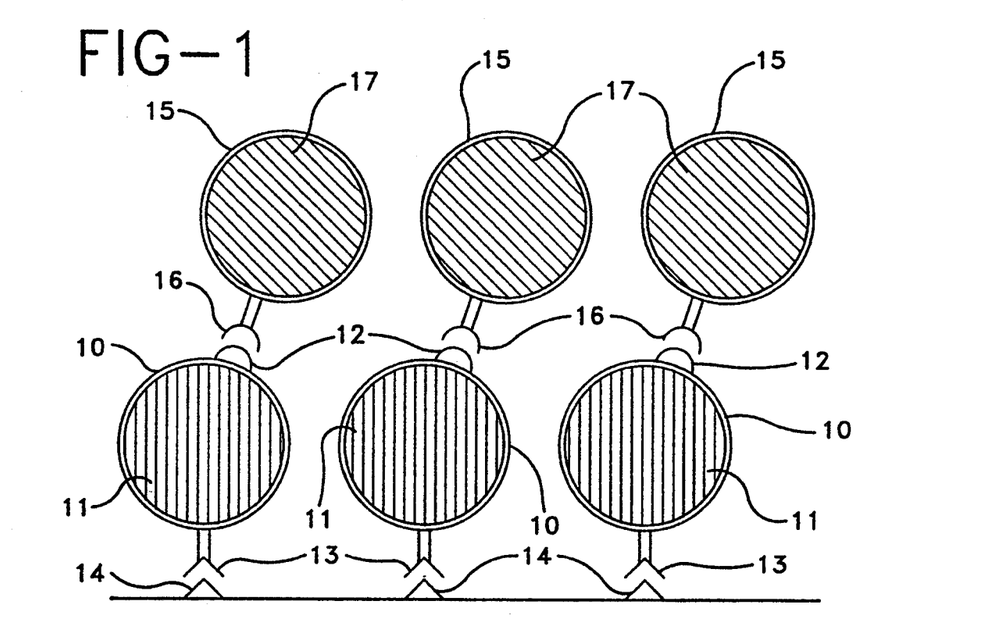
FIG. 1 is a schematic representation of an assay using a tracer with a first labeled liposome conjugate which binds a second labeled liposome conjugate.
Figure 2:
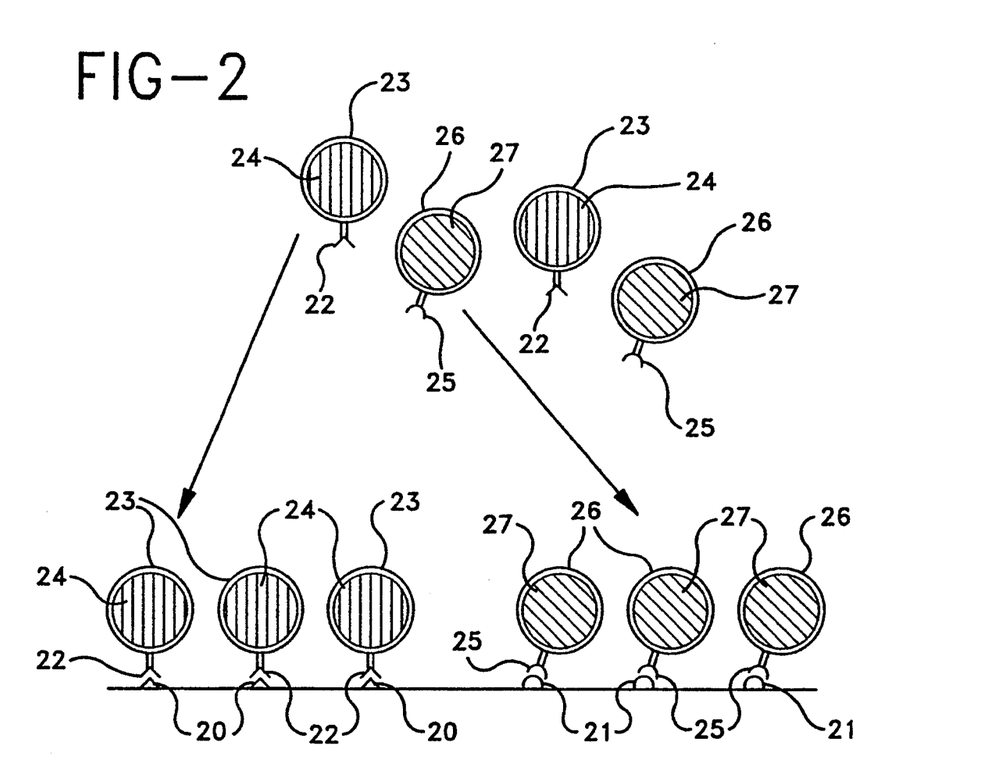
FIG. 2 is a schematic representation of an assay using a tracer with different labeled liposome conjugates which bind to different binders.
Figure 3:
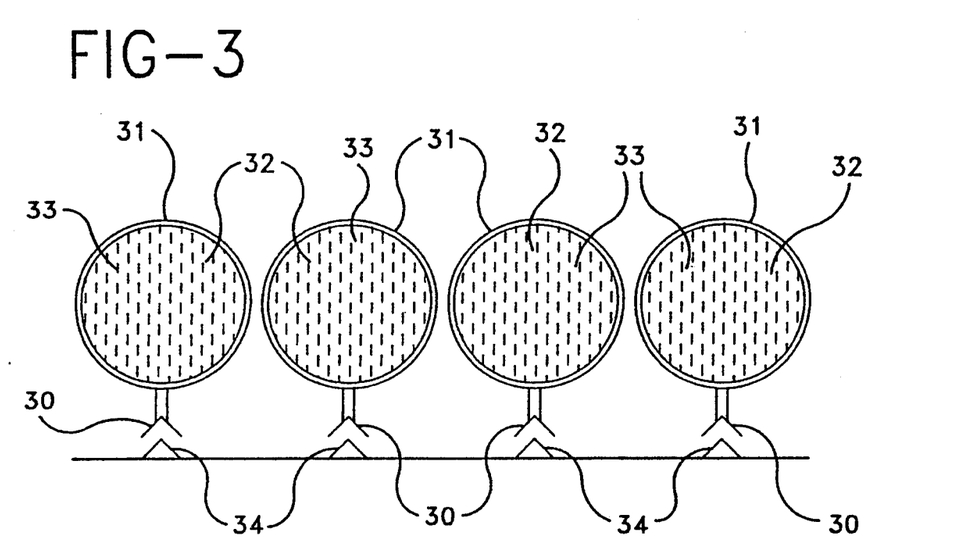
FIG. 3 is a schematic representation of an assay using a tracer with a liposome conjugate with one particulate label and two detectable substances.

At least two different detectable substances may be present in the tracer in different ways. The tracer may include a first particulate label with at least one ligand, the first particulate label including a first detectable substance, and a second particulate label with a second ligand that binds to a ligand on the first particulate label, the second particulate label including a second detectable substance which is different than the first detectable substance, as illustrated in FIG. 1. The tracer may include at least two different ligands, each ligand labelled with a particulate label containing a different detectable substance for each type of ligand as illustrated in FIG. 2. The tracer may include one ligand with a particulate label which contains at least two different detectable substances as illustrated in FIG. 3.

The labels are detected after the tracer is bound to the binder or the tracer is bound to at least one analyte bound to the binder.

Some advantages of this assay are enhanced sensitivity, the ability to detect more than one analyte at the same time, the elimination of confusion between reagents, and the ability to simultaneously detect more than one wavelength at the same time in instrumental analysis allowing greater discrimination of signal above noise. The invention also provides an assay tool which can be tailored for many different types of assays.

For a better understanding of the present invention, together with other and further objects, reference is hereby made to the following description, taken together with the accompanying drawings, and its scope will be pointed out in the appended claims.

DETAILED DESCRIPTION OF THE INVENTION

The material used as a binder is selected for the particular assay chemistry involved, considering the analyte to be assayed and the specific assay procedure, e.g., competitive, sandwich. Preferably, the binder is a specific binding species comprising one member of a specific pair, e.g., an antigen or antibody. Selection of a suitable binder is within the scope of those skilled in the art.

The type of binder to be used is dependent upon the analyte to be assayed and the specific assay procedure. The binder may be an antibody, including serum, polyclonal or monoclonal antibodies, an antigen, a protein specific for the material to be bound, or a naturally occurring binder. Thus, for example, in a competitive type assay for an antigen or hapten, the binder may be an antibody or a naturally occurring substance which is specific for the tracer and antigen or hapten. If the assay is for an antibody, then the binder may, for example, be an antigen or an antibody which is specific for the antibody to be assayed. In a sandwich type assay, wherein the analyte is an antibody, the binder may be an antigen for the antibody, or a protein such as protein A which selectively binds Fc fragments of certain antibodies. In a sandwich assay, if the analyte is an antigen, e.g. having more than one epitope or determinant site, then the binder may be an antibody or naturally occurring binder which is specific for the antigen to be assayed.

A binder is used in an assay in supported form. The support may be porous or non-porous. Porous and non-porous supports are well known to those skilled in the art. Similarly, the methods for securely attaching a binder to a solid support are well known to those skilled in the art. Thus, the binder may be attached through covalent or non-covalent bonding, directly or indirectly. Preferably the binder is adsorbed to a solid support.

Supports include a wide variety of materials known to be suitable as supports for a binder in an assay. Non-limiting representative examples include nitrocellulose, polymers such as nylon or latex, glass particles, etc. The solid support may be in a variety of forms, including sheets, tubes, cards, test strips, microtiter plates, etc.

The solid support is one which has a surface area (area/unit weight of material) such that the binder can be supported on the support in a concentration (weight/unit area) such that the tracer is detectable under assay conditions. Detectable means either that the label can be seen with the naked eye or can be detected with an apparatus such as a spectrophotometer or fluorometer.

An analyte is detected in an assay with the use of a tracer. Preferably, the tracer is comprised of a specific binding portion coupled to a particulate label. Thus if the tracer is to be used in a competitive antibody/antigen assay, the specific binding portion would be the analyte or an appropriate analog thereof. If the assay is a sandwich antigen/antibody assay, the specific binding portion would specifically bind the analyte. Those skilled in the art will also appreciate that the tracer system may further comprise amplification systems. Thus under assay conditions the tracer may bind to the analyte in an indirect manner rather than directly.

The preferred tracer has at least one particulate label coupled to at least one ligand, the particulate label containing at least one detectable substance, the total tracing system including at least two detectable substances.

The choice of ligand to be labeled for use as a tracer depends on the analyte to be assayed and the assay procedure. The ligand is a substance capable of being bound by a binder. Ligands include antigens (e.g. proteins, polysaccharides, nucleic acids, peptide hormones, steroids, drugs, bacteria, viruses, tumor antigens, enzymes, vitamins); haptens; and antibodies (polyclonal and monoclonal). Non-limiting examples of antigens (or their corresponding antibodies) which may be assayed using the present invention include malaria, Streptococcus, influenza, rubella, meningococcus, Candida, respiratory syncytial virus, HIV, tumor markers, digoxin, theophylline, ferritin, FSH, LH, prolactin, testosterone, progesterone, HCG, TSH, T4, T3.

The particulate label is a colored particle with a diameter of from about 0.01 $\mu$m to about 10 $\mu$m. The colored particle may be solid or solid-like, as opposed to non-solid soluble labels such as radioisotopes and enzymes. Solid-like particulate labels include vesicles, microcapsules and stabilized colloidal particles.

A preferred particulate label is a sac which includes a substance whereby the tracer when used in the assay is detectable. The sac which is used as the particulate label may be any one of a wide variety of sacs, including but not limited to liposomes (singled walled or multi-lamellar), polymer microcapsules, for example those made by coacervation or interfacial polymerization, and stabilized colloidal particles.

Liposomes can be prepared from a wide variety of lipids, including phospholipids, glycolipids, steroids, relatively long chain alkyl esters; e.g. alkyl phosphates, fatty acid esters; e.g. lecithin, fatty amines, and the like. A mixture of fatty materials may be employed, such as a combination of neutral steroid, a charged amphiphile and a phospholipid. Illustrative examples of phospholipids include lecithin, sphingomyelin, and dipalmitoyl phosphatidylglycerol. Representative steroids include cholesterol, cholestanol, lanosterol, and the like. Representative charge amphiphilic compounds generally contain from 12 to 30 carbon atoms. Mono- or dialkyl phosphate esters or alkyamines; e.g. dicetyl phosphate, stearyl amine, hexadecyl amine, dilaurylphosphate, and the like are representative.

The preferred detectable substance used in the particulate label is a visible substance, more preferably, a dye. Dyes are chemical compounds which have color due to the interaction of light with the electron system of the molecule. Dye molecules may have ionizable groups called auxochromes, e.g. —$NH_2$, —OH, through which the chromophore can bind to a target molecule. Dyes may contain no anionic or cationic groups, such as 4-(dicyanomethylene)- 2-methyl-6-(p-dimethylaminostyryl)-4H-pyran, or may consist of polycyclic rings, such as pyrene, or may consist of aromatic rings connected by conjugate alkyl chains, such as 1,6-diphenyl-1,3,5-hexatriene. Unsaturated chromophoric groups may be responsible for the color, e.g. —$NO_2$, —N=N— and =CO, i.e, quinoid rings, xanthenes, azines, thiazines, azos, nitros, triarylmethanes, acridines and many others. Non-limiting examples of the dyes include sulforhodamine B (a xanthine amino dye with a red fluorochrome) light green SF yellowish (an anionic triphenylmethane dye), chrome azurol S (a triphenylmethane dye), brilliant blue FCF (a blue acid triphenylmethane dye), and nile red (a fat-soluble, solvent oxazone dye). The dyes may be water soluble or lipophilic.

The dye concentration is adjusted by methods known to those skilled in the art according to the solubility properties of the dye and optimized for the desired detection as well as for stability.

The preparation of sacs containing dye for immunoassay is described in U.S. Pat. No. 4,695,554, the entire disclosure of which is herein incorporated by reference.

Although the dye used in the sac is an absorbing dye, such dyes may also have fluorescent properties. Therefore, within the scope of the invention, the dyes may be detected by fluorescence rather than by absorption characteristics.

Representative examples of other detectable substances which may be employed include ferritin, phycoerythrins or other phycobiliproteins; organometallic complexes, e.g., phthalocyanines, porphyrins, lanthanide chelates; fungal, algal or bacterial pigments or derivatives such as bacterial chlorophylls; plant materials or derivatives, and the like.

The liposomes sacs may be prepared in an aqueous solution of colored substance and as a result the substance is incorporated into the liposome. The liposomes sacs may be prepared by vigorous agitation in the solution, followed by removal of unincorporated colored substance from the exterior of the sac. Further details with respect to the preparation of liposomes are set forth in U.S. Pat No. 4,342,826 and PCT International Publication No. WO80/01515, both of which are incorporated by reference.

Detectable substances may also be attached or covalently linked to the surface of the liposome using surface chemistries known to those skilled in the art and similar to the way antibodies are coupled to liposomes as described in Example 1. Liposomes may also be prepared using a lipophilic dye included in a bilayer by dissolving the lipophilic dye with the other film components in the preparation of the film which is swollen to make the liposomes.

Procedures for coupling the specific binding portion or ligand with a particulate label are well known in the art. Such techniques include absorption, covalent bonding, derivatization, activation, and the like. In producing a tracer where the specific binding portion is labeled with a sac, the sac may be produced from a component which has been derivatized with the specific binding portion whereby the sac when produced is sensitized with a specific binding portion. In another procedure, the sac including a colored substance may be initially formed, followed by sensitizing the sac with the specific binding portion by procedures known in the art.

In forming a tracer, a sac may be coupled to a ligand by the use of an appropriate coupling or spacer compound which does not destroy the immunoreactivity of the ligand. Alternatively, the sacs may be coupled directly to the ligand by procedures known in the art. The sacs may also be sensitized with the ligand by either coupling the ligand to one of the materials to be used in forming the sacs or by coupling the ligand to the sacs after they are formed.

In assays, the binder is a binder for both analyte and tracer, or a binder is a binder for only one of the analyte and tracer, with the type of binder which is employed being dependent upon the assay which is to be used for determining the analyte. Thus, for example, if the assay is a sandwich assay, the binder is a binder for only the analyte. In this type of assay, the tracer is specific for the analyte so that tracer is bound to analyte which binds to binder. In an inhibition assay or competitive assay, the binder is specific for both tracer and analyte. In this type of assay, the presence of analyte inhibits the binding of tracer to the binder. Thus, the tracer, for example, when bound to the solid support is either directly bound to the binder on the support or is bound to analyte which is bound to binder on the solid support.

It has been discovered that encapsulating more than one dye, in different sacs or in the same sac, increases the usefulness of labeled sacs in performing immunoassays.

Referring now to the figures, in one embodiment shown in FIG. 1, a first liposome is conjugated with a first antibody to antigen A. The first liposome (10) encapsulates a first dye (11) and bears a detectable marker (12) on its surface, for example, a hapten or determinants (epitopes) on the antibody itself. The first liposome is conjugated with an antibody (13) to an antigen (14). A second liposome (15) is conjugated with a second antibody (16) specific to the marker (12) on the first liposome (10). The second liposome encapsulates a second dye (17) which is different from, and preferably complementary to, the first dye. When the first and second liposomes are used in a tracer in an assay, there is enhancement of the signal for antigen A with no confusion between reagents. The detection of antigen A results in a different color than either of the solutions.

In another embodiment shown in FIG. 2, two different antigens represented by (20) and (21), are detected simultaneously using a mixture of liposomes which encapsulate different dyes. A first antibody (22) to antigen (20) is conjugated with a liposome (23) encapsulating a first dye (24). A second antibody (25) to antigen (21) is conjugated with a liposome (26) encapsulating a second dye (27). The presence of either antigen (20), antigen (21) or the presence of both antigens (20) and (21) can be detected by the generation of a different color for each case. The assay may be carried out on a support such as nitrocellulose using a single reagent mixture. Through a choice of dyes, essentially any color can be produced.

In yet another embodiment illustrated in FIG. 3, an antibody, antigen or hapten (30) which binds to its counterpart (34) is conjugated with a liposome (31) encapsulating a minimum of two dyes (32) and (33). This allows for the provision of liposomes of any desired color through the choice of dyes which complement each other. In instrumental analysis, analyte can be detected by simultaneous measurement at more than one wavelength, resulting in greater discrimination of signal above noise. In addition, adequate signal will be generated from dyes which would not have sufficient absorbance if encapsulated singly.

The use of more than one dye allows many variations. Complementary colored dyes can be balanced with respect to absorbance across the visible spectrum, resulting in a black hue. Alternately, a first liposome encapsulating a first dye can be used to both saturate nonspecific sites and provide a color background. Binding of a second liposome encapsulating a second balancing dye at specific sites can result in a black color so that contrast at specific sites and signal are increased.

EXAMPLE 1

TRACER PREPARATION

A. Liposome Preparation
1. To a 2000 ml round-bottom rotoevaporator flask, add:
    a: 1.018 grams cholesterol (Sigma CH-PL)
    b: 1.88 grams distearoyl phosphatidylcholine (Avanti Polar Lipids 3850365)
    c: 206 mg distearoyl phosphatidyl glycerol (Avanti Polar Lipids)
    d: (75 mg crosslinking agent ((N-maleimido)caproyl-distearoyl phosphatidylethanolamine; Becton Dickinson Advanced Diagnostics, Baltimore, Md.)
    e: 150 ml chloroform (Fisher)
2. Swirl to mix.
3. Place on rotoevaporator with the following settings:
    Water bath temperature=40° C.
    Rotation speed=4
4. Slowly increase vacuum until a film forms.
5. Reduce pressure to 200 millibar. Allow to rotate at a medium rate for 30 minutes.
6. Lyophilize overnight.
7. On a rotoevaporator add 150 ml distilled water and rotate at 60° C. without vacuum until the lipid film is in suspension.
8. Shell freeze in a dry ice/methanol bath.
9. Lyophilize to a dry powder.

B. Preparation of Liposome Particulate Labels—Single Dye

1. Prepare colored solution of:
   a. Sulforhodamine B (5.6% (weight/volume) in 5 mM sodium acetate-5 mM EDTA pH 4.5).
   b. Light green SF yellowish (20% (weight/volume) in 5 mM sodium acetate-5 mM EDTA pH 4.5).
2. To two 80 mg. amounts of liposome powder as described in Example 1A, 10 ml of colored solutions Sulforhodamine B and Light Green SF Yellowish are separately added. Warm the liposome/dye suspension at 60° C. for 30 minutes with intermittent shaking.
3. Separately extrude the two warm liposome preparations through 1.0 μm, 0.4 μm, and then 0.2 μm polycarbonate membranes (Nuclepore).
4. Separate free colored material from the liposome suspensions on Sepharose 6 Fast Flow chromatography columns (Pharmacia) equilibrated in 50 mM sodium acetate buffer pH 4.5 with 1 mM EDTA and 50 mM NaCl.
5. Separately store the two dye-encapsulated liposome preparations in the buffer specified in step 4.

C. Coupling of Liposome Particulate Label to Specific Binding Species: Green Particulate Label
1. 0.8 mg goat anti-biotin (Sigma) was dialyzed against phosphate buffered saline (pH 7.4).
2. React with 3-(2-pyridyldithio)propionic acid N-hydroxysuccinimide ester (SPDP) (Sigma) at a 3:1 molar ratio of SPDP:antibody for 30 minutes at room temperature with stirring.
3. Add 1/10th volume 1M sodium acetate pH 4.5 and stir for about 20 seconds.
4. Add 1/100th volume 1M dithiothreitol and stir at room temperature for 30 minutes.
5. Remove dithiothreitol by passing the reaction volume over a Sephadex G-25 medium column equilibrated with Tris buffer (50 mM Tris, 50 mM sodium acetate, 50 mM NaCl, 1 mM EDTA, pH 8.0).
6. Monitor the O.D. 280 and pool fractions containing protein.
7. Adjust the pH of 4 ml of the green liposomes prepared above in B to 8.0 with 1M Tris, pH 10. Mix the antibody pool with the liposomes at a coupling ratio of 1 mg derivatized antibody: 40μ moles Pi.
8. React overnight at room temperature.
9. Separate coupled product on Sepharose 6 Fast Flow chromatography column (Pharmacia) equilibrated in 30 mM 3-[N-morpholino]-2-hydroxypropanesulfonic acid (MOPSO)—10 mM EDTA—0.2% sodium azide—0.05% dimethylsulfoxide (DMSO)—1.8% glycerol—pH 6.8.
10. Collect and pool void volume fraction.
11. Store at 4° C.

D. Coupling of Liposome Particulate Label to Specific Binding Species: Sulforhodamine B Particulate Label
1. 0.6 mg Affinity purified rabbit antibody to Group A Streptococcus (n-acetylglucosamine-agarose column) is dialyzed against phosphate buffered saline (100 mM, pH 8).
2. React with SPDP (Sigma P-3415) at a molar ratio of 3:1 (SPDP:antibody) for 30 minutes at room temperature with stirring.
3. Add 1/100th volume of 1M dithiothreitol and stir for 60 seconds.
4. Add 1/10th volume of 1M sodium acetate pH 4.5 and stir for 30 minutes.
5. Remove dithiothreitol by passing the reaction volume over a Sephadex G25 column equilibrated with Tris buffer (50 mM Tris, 50 mM sodium acetate, 50 mM NaCl, 1 mM EDTA, pH 8.0).
6. Monitor the absorbance at 280 nm and pool fractions containing protein.
7. Adjust the pH of sulforhodamine-containing liposomes (described above in B) to 8.0 with 1M Tris pH 10. Mix the antibody pool with the liposomes at 1 mg derivatized antibody per 20 μmoles phosphorus.
8. React overnight at room temperature.
9. Separate coupled product from free antibody on a Sepharose 6 Fast Flow chromatography column (Pharmacia) equilibrated with MOPSO-glucose buffer (30 mM MOPSO—10 mM EDTA—0.2% sodium azide—0.05% DMSO—1.2% glycerol—100 mM glucose, pH 6.8.)
10. Collect and pool void volume fractions.
11. Store at 4° C.

EXAMPLE 2

ASSAYS

The tracers prepared in Example 1C (anti-biotin antibody conjugated with light green liposome) and Example 1D (anti-Group A Streptococcus antibody conjugated with Sulforhodamine B liposome) were tested against the antigens biotin and group A Streptococcus. The biotin antigen was attached to nitrocellulose paper by means of biotinylated antibody (2 μL, 20 μg/ml in 0.1% blotto in 0.1M sodium phosphate, pH 7). Group A Streptococcus (2 μL, heat-killed, with 0.2% sodium azide preservative) was attached to the nitrocellulose membrane by means of anti-Group A Streptococcus antibody.

The assay procedure was as follows:

A. 1. Three drops (approximately 150 μl) of the solution containing anti-Group A Streptococcus-sulforhodamine B liposome tracer (0.87 μmP/ml) were added and allowed to flow through to the test area of Group A Streptococcus.

The test area was then washed by the addition of three drops of wash buffer (1M guanidine HCl buffer, pH 7).

The results were then read by visually observing the presence of a distinctive pink color on the test area. A strong positive pink signal resulted.

2. Three drops (approximately 150 μl) of anti-biotin-light green liposome tracer (0.6 μmP/ml) were added to the test area dotted with biotinylated antibody on top of a 0.8 μm pad and allowed to absorb.

The test area was then washed with 1M guanidine HCl buffer.

The results were read by visually observing the presence of a distinctive green color on the test area. A strong positive green signal resulted.

B. Mixed liposomes

Equal amounts of the anti-Group A streptococcus-sulforhodamine B liposome tracer prepared in Example 1D and the anti-biotin-light green liposome tracer prepared in Example 1C were mixed. The mixture appeared bluish-purple.

The liposome mixture was split in half. Half the volume (150 μl) was used in an assay for Group A Streptococcus as described in Example 2(B)(1) above. Pink signal only developed.

The other half of the mixture (150 µl) was used in an assay for biotin. as described in Example 2(B)(2) above. Green signal only developed.

This experiment showed that individual specificities and colors can be pulled out of a liposome mixture to differentiate between analytes.

EXAMPLE 3

TRACER PREPARATION—MIXED DYES

A. Preparation of Mixed Dyes

Dye mixtures were prepared in dye buffer (5 mM Na acetate, 5 mM EDTA, pH 4.5).

1. A dye mixture of 20% light green SF yellowish—5.6% sulforhodamine B was prepared by mixing 4 grams light green SF yellowish, 1.12 grams sulforhodamine B and 2 ml 10X dye buffer with the addition of distilled water to a volume 20 ml and stirring at room temperature. The pH was adjusted to 4.5.
2. A dye mixture of 6% chrome azurol—0.1% sulforhodamine B—1.65% light green SF yellowish was prepared by mixing 1.2 grams chrome azurol S, 0.02 grams sulforhodamine B, 0.33 grams light green SF yellowish and 2 ml 10X dye buffer with the addition of distilled water to a volume of 20 ml with stirring at room temperature. The pH was adjusted to 4.5.

The dye mixtures were separately filtered through Falcon bottle top filters which had been washed with 100 ml distilled water. The osmolality of the 20% light green—5.6% SRB was 752 mOsm. The osmolality of the 6% chrome azurol-0.1% SRB-1.65% light green was 418 mOsm.

B. Tracer Preparation

1. Two separate 80 mg portions of the frozen liposome powder prepared in Example 1A were weighed out into separate 50 ml conical tubes.
2. To one liposome portion was added 10 ml of the dye mixture of Example 3A(1), to the other liposome portion was added 10 ml of the dye mixture prepared in Example 3A(2).
3. Swirl to dissolve.
4. Warm at 60° for 30 min.
5. Each of the two liposome preparations was separately extruded through 1.0 µm, 0.4 µm then 0.2 µm membranes (Nucleopore PC membranes 47 mm: #11110, #111107 and #111106, respectively) then warmed and reextruded through a fresh 0.2 µm filter.
6. Buffers for the Sepharose 6 Fast Flow columns were prepared by adjusting the osmolality of the column wash buffer with glycerin to the osmolality of the dye mixtures.
   a. For 6% chrome mixture: Added about 5 ml glycerol to 500 ml column wash buffer (pH 4.5) to adjust to 400±50 mOsm.
   b. For light green-SRB mixture: Added about 8 ml glycerol to 500 ml column wash buffer (pH 4.5) to adjust to 700±50 mOsm.
   A Fast Flow column was equilibrated with each buffer.
7. The separate liposome preparations were separated from free dye on the Fast Flow Sepharose 6 columns.
8. After this separation, uncoupled liposomes were pooled in separate groups for the two dye mixtures.

EXAMPLE 4

SPECTRAL SCAN OF ENCAPSULATED MIXED DYES

Liposomes prepared in Example 3 and containing light green SF yellowish-Sulforhodamine B dye mixture were diluted 1:50 in 0.5% sodium dodecyl sulfate (SDS) and warmed at 58° C. for 30 minutes.

Dye Mixture of light green SF yellowish-sulforhodamine B as prepared in Example 3 was diluted 1:8000 in phosphate buffered saline (PBS), pH 7.5, and in 0.5% SDS.

Liposomes prepared in Example 3 and containing chrome azurol-sulforhodamine B dye mixture were diluted 1:13.5 in 0.5% SDS and warmed at 58° for 30 minutes.

Dye mixture of chrome azurol-sulforhodamine B dye as prepared in Example 3 was diluted 1:1000 in PBS, pH 7.5 and in 0.5% SDS.

Figure 4:
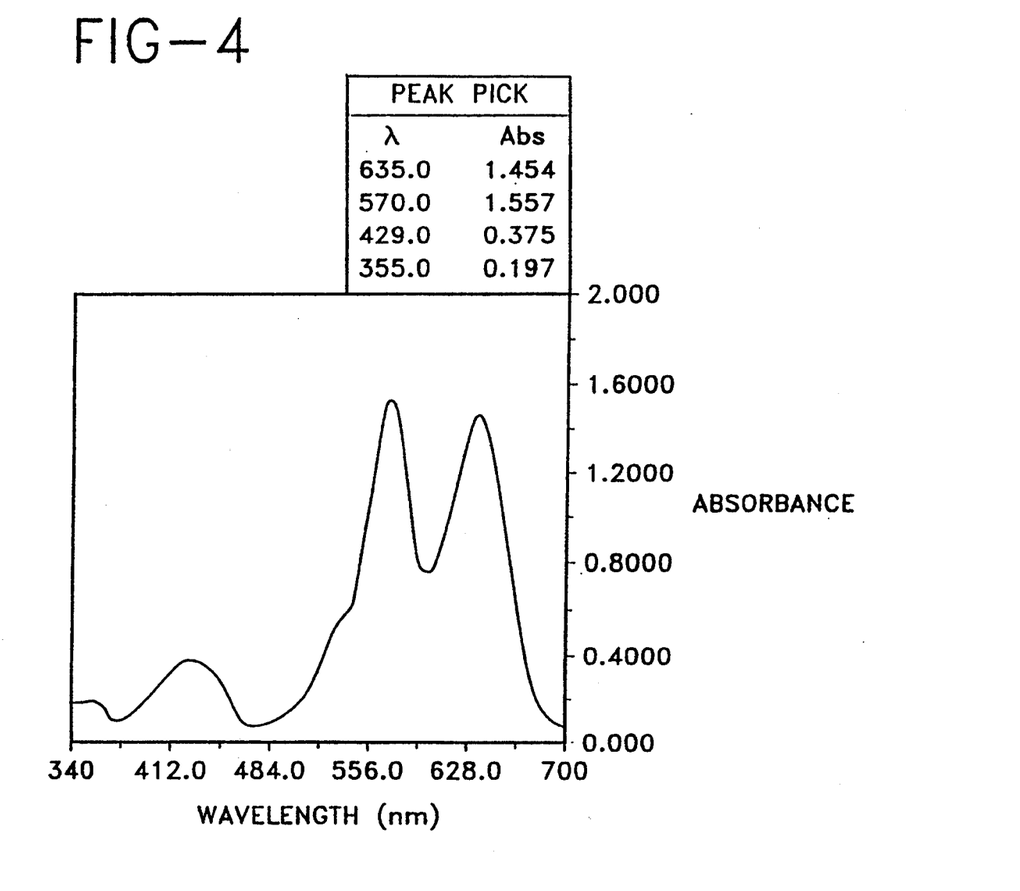
FIG. 4 is a graph representing an absorbance scan of liposomes containing light green-SRB that were lysed in 0.5% SDS.
Figure 5:
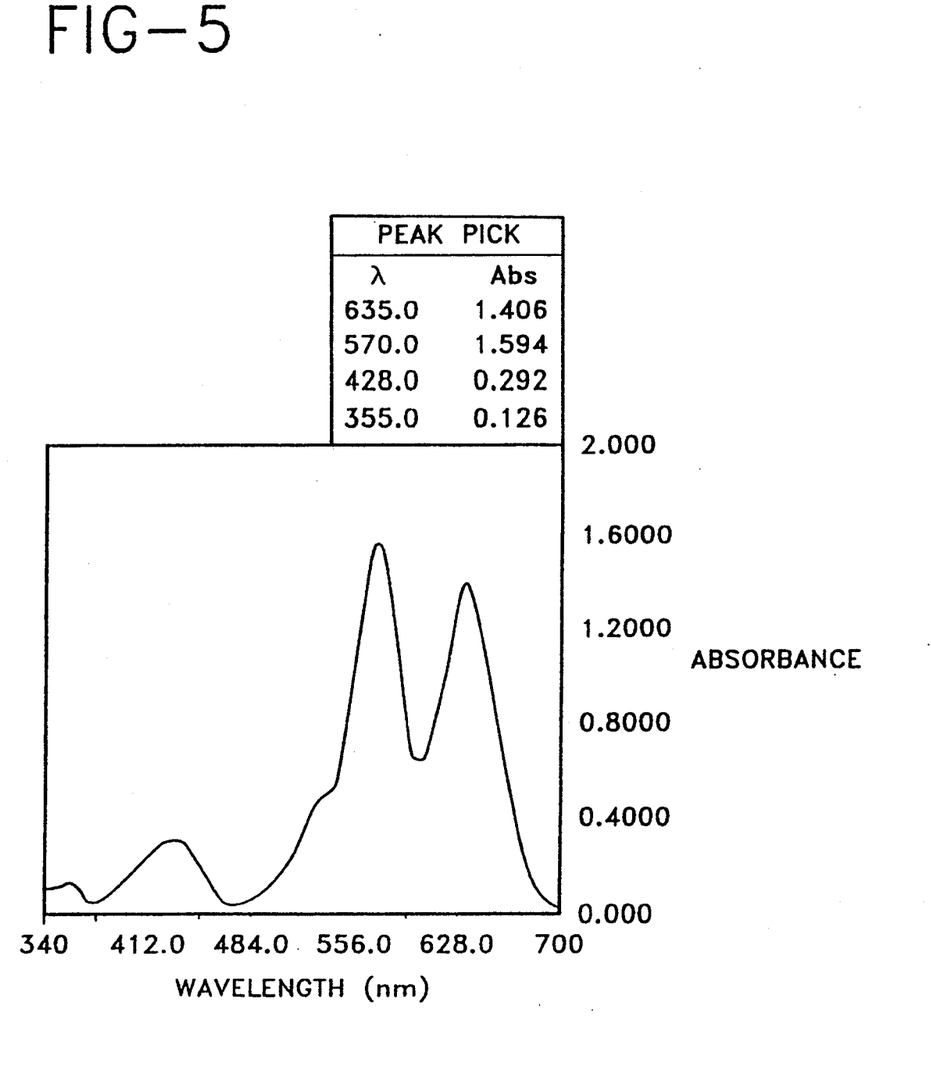
FIG. 5 is a graph representing an absorbance scan of light green-SRB dye mixture in 0.5% SDS.
Figure 6:
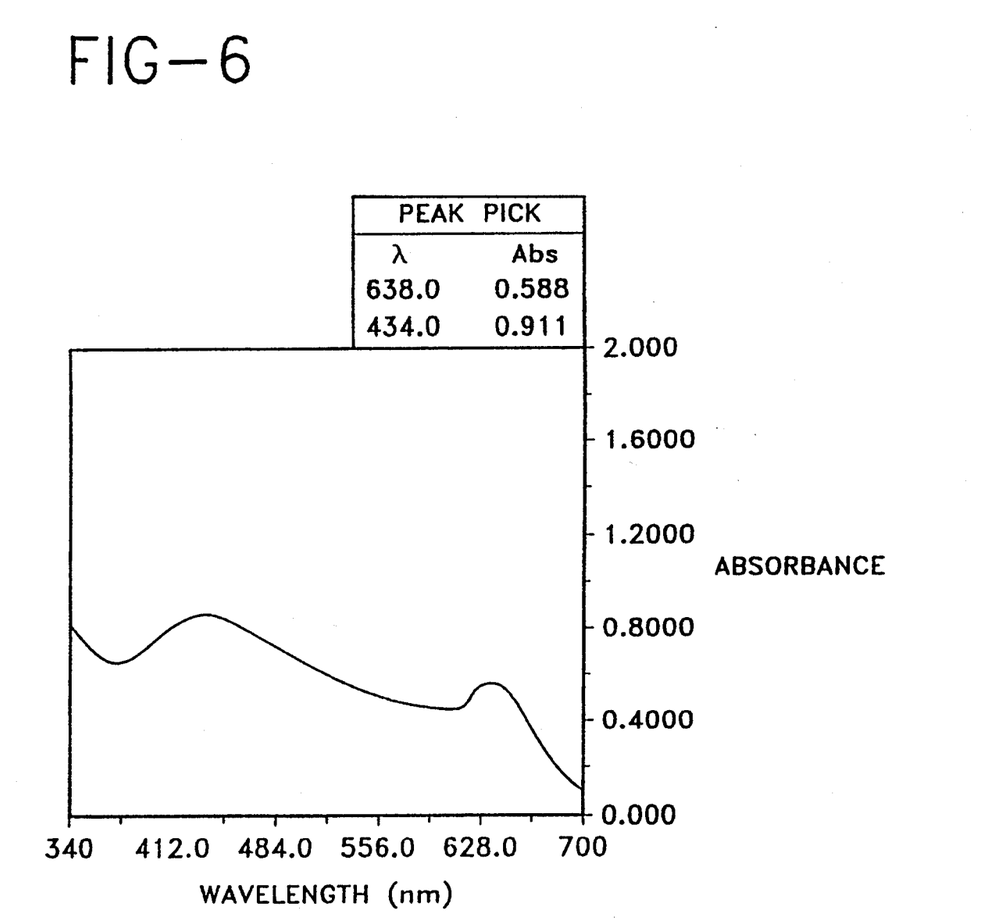
FIG. 6 is a graph representing an absorbance scan of lysed liposomes that contained chrome azurol-SRB-light green.
Figure 7:
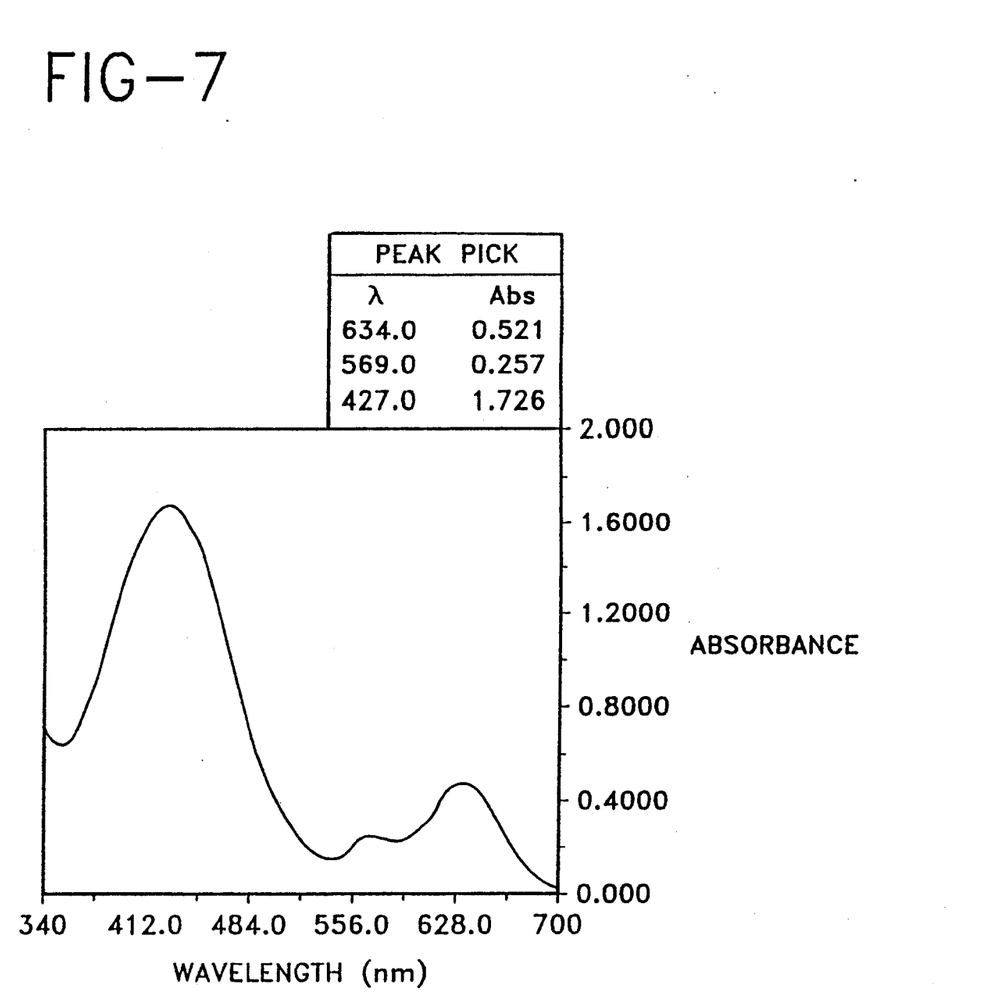
FIG. 7 is a graph representing an absorbance scan of chrome azurol-SRB-light green dye mixture in PBS.
Figure 8:
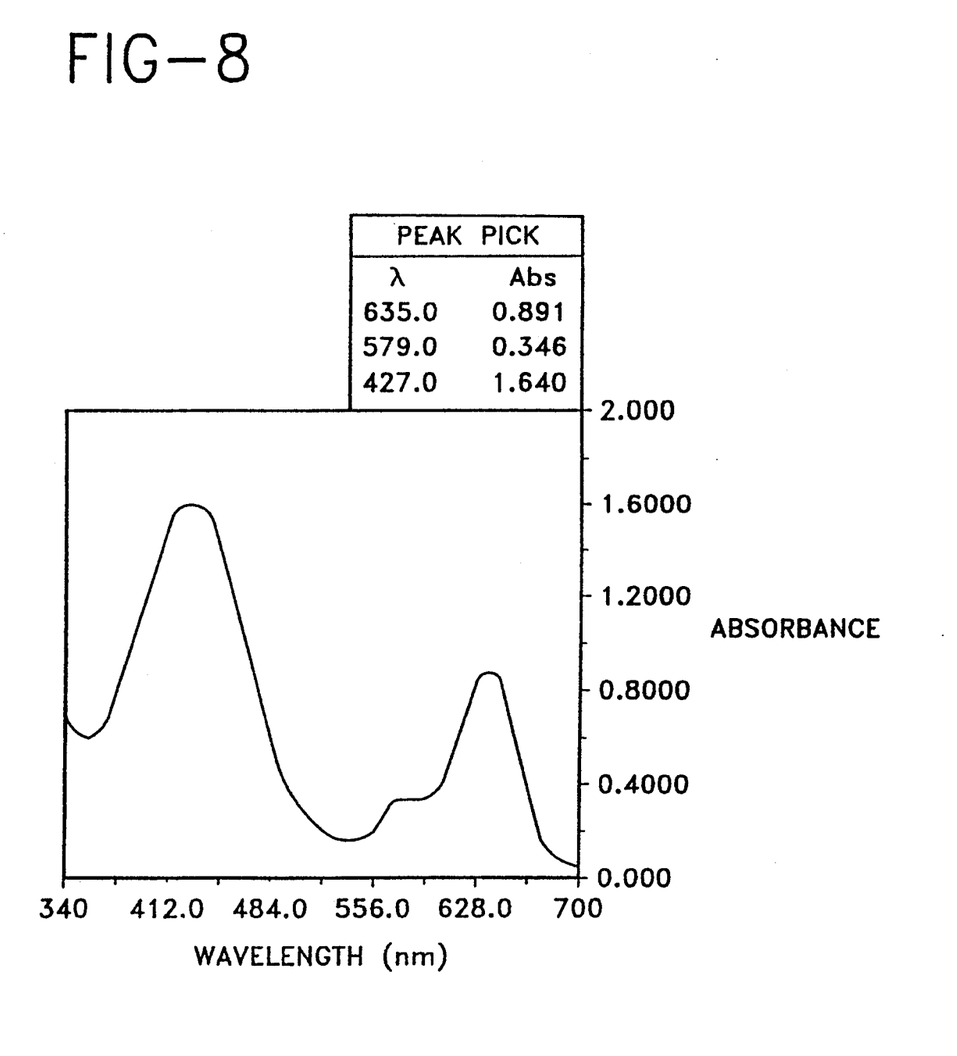
FIG. 8 is a graph representing an absorbance scan of chrome azurol-SRB-light green dye mixture in SDS.

Each dye mixture and each lysed liposome preparation was scanned from 340 nm to 700 nm using a Beckman DU7. Results are shown in FIGS. 4–8. FIG. 4 shows the scan of the lysed liposomes containing light green-SRB. FIG. 5 shows the scan of the light green SRB dye mixture alone. FIG. 6 shows the scan of the lysed liposomes containing chrome azurol-SRB-light green. FIGS. 7 and 8 show scans of the chrome azurol-SRB-light green dye mixture in PBS and in 0.5% SDS, respectively. The correspondence of the scans of dye mixtures alone to liposome preparations shows that the dye mixtures were successfully encapsulated by the liposomes and that each dye can be separately identified in a mixture of dyes.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A process for the assay of a sample, suspected of containing at least one analyte, comprising:
   1) contacting said sample with a binder and a tracer, wherein said binder
      is immobilized on a solid support, and
      specifically binds to said at least one analyte, and
      wherein said tracer comprises
      a first particulate label which includes a first detectable substance and which has a first and second ligand immobilized thereon, wherein said first ligand specifically binds to either said binder or said at least one analyte, and
      a second particulate label which includes a second detectable substance and which has a third ligand immobilized thereon, wherein said third ligand specifically binds said second ligand on said first particulate label,
      under conditions such that said tracer becomes bound to said binder in proportion to the amount of said at least one analyte in said sample; and
   2) detecting said first and second detectable substances as a measure of the amount of said at least one analyte in said sample.

2. An assay composition for use in the method of claim 1 comprising a tracer, wherein said tracer comprises a first particulate label which includes a first detectable substance and which has a first and second ligand immobilized thereon, wherein said first ligand specifically binds to either said binder or said at least one analyte, and a second particulate label which includes a second detectable substance and which has a third ligand immobilized thereon, wherein said third ligand specifically binds said second ligand on said first particulate label.

* * * * *